United States Patent [19]

Menken

[11] Patent Number: 4,819,643

[45] Date of Patent: Apr. 11, 1989

[54] METHOD AND APPARATUS FOR CARDIOVERTER/PACER FEATURING A BLANKED PACING CHANNEL AND A RATE DETECT CHANNEL WITH AGC

[75] Inventor: John Menken, Champlin, Minn.

[73] Assignee: Mieczyslaw Mirowski, Owings Mills, Md.

[21] Appl. No.: 931,854

[22] Filed: Nov. 18, 1986

[51] Int. Cl.[4] .................... A61N 1/00; H05G 00/00
[52] U.S. Cl. ....................... 128/419 P; 128/419 PG; 128/419 D
[58] Field of Search ........ 128/419 P, 419 PG, 419 D, 128/696, 704, 705

[56] References Cited

U.S. PATENT DOCUMENTS

| | | | |
|---|---|---|---|
| 3,543,050 | 11/1970 | Paine | 128/696 |
| 3,717,153 | 2/1973 | Bowers | 128/419 P |
| 3,903,874 | 9/1975 | Shakespeare | 128/696 |
| 3,985,142 | 10/1976 | Wickham | 128/419 PG |
| 3,999,557 | 12/1976 | Citron et al. | 128/419 PG |
| 4,114,628 | 9/1978 | Rizk | 128/419 PG |
| 4,263,915 | 4/1981 | McDonald et al. | 128/419 PG |
| 4,266,551 | 5/1981 | Stein | 128/419 PG |
| 4,305,396 | 12/1981 | Wittkampf et al. | 128/419 PG |
| 4,344,437 | 8/1982 | Markowitz | 128/419 PG |
| 4,379,459 | 4/1983 | Stein | 128/419 PG |
| 4,393,877 | 7/1983 | Imran et al. | 128/419 D |
| 4,401,119 | 8/1983 | Herpers | 128/419 PG |
| 4,407,288 | 10/1983 | Langer et al. | 128/419 D |
| 4,421,114 | 12/1983 | Berkovits et al. | 128/419 PG |
| 4,440,172 | 4/1984 | Langer | 128/419 D |
| 4,458,691 | 7/1984 | Netravali | 128/705 |
| 4,458,692 | 7/1984 | Simson | 128/705 |
| 4,467,810 | 8/1984 | Vollmann | 128/419 PG |
| 4,510,945 | 4/1985 | Barreras | 128/696 |
| 4,531,523 | 7/1985 | Anderson | 128/696 |
| 4,557,266 | 12/1985 | Schober | 128/419 PG |

Primary Examiner—Francis J. Jaworski
Assistant Examiner—George Manuel
Attorney, Agent, or Firm—Fleit, Jacobson, Cohn & Price

[57] ABSTRACT

The implantable cardioverter/pacer includes a pacer channel and a rate detect channel both receiving a cardiac signal representative of the ECG of patient. The pacing channel issues a pacing signal when the amplitude of the cardiac signal fails to exceed a first predetermined threshold within a predetermined time period. The rate detect channel has a variable gain amplifier which is controlled by an automatic gain control (AGC). The AGC increases the gain in the amplifier based upon the level of the cardiac signal applied thereto and upon the time since the last peak of the cardiac signal. A one shot receives the output of the variable gain amplifier and produces a heart rate signal. Both the pacing and the heart rate signals are applied to a microprocessor. The microprocessor ignores or blanks out the first two or three pacing signals in order to allow the automatic gain control in the rate detect channel to increase or approach a maximum in order to determine whether a low level cardiac signal is present which may be indicative of certain ventricular arrhythmias. After the blanking period, the microprocessor issues appropriate treatments, either pacing or cardioverting, to the heart.

17 Claims, 3 Drawing Sheets

METHOD AND APPARATUS FOR CARDIOVERTER/PACER FEATURING A BLANKED PACING CHANNEL AND A RATE DETECT CHANNEL WITH AGC

BACKGROUND

The present invention relates to an implantable device which senses abnormal heart beat rates and delivers stimulating electrical pulses to the heart in order to correct such abnormalities. Particularly, the present invention relates to a pacer/cardioverter that is capable of detecting arrhythmias requiring pacing and also ventricular fibrillation, and of providing the appropriate treatments, and a corresponding method of such detecting and treating a heart.

It is well known that the heart can be monitored by sensing the electrical activity thereof. Many processing schemes have been devised to determine the condition of the heart and to particularly determine whether the heart is beating at an abnormally slow rate (bradycardia), a normal rate (normal sinus rhythm), an abnormally fast rate (tachycardia), a generally chaotic fast rate (ventricular fibrillation), or has substantially ceased to beat (asystole).

The electrical activity of the heart can be sensed and the resultant signal pre-processed (for example, by pre-amplification, filtering, etc.), and then digitized in some fashion. The digitized signal can further be processed to specifically diagnose the condition of the heart. These operations can occur in an implantable device. Based upon the diagnosis, stimulating pulses are applied to the heart from the implantable device. The stimulating pulses may consist of pacing pulses, a low level electrical shock pulse, or a high level electrical shock pulse. The low and high level shock pulses are called herein "cardioverting pulses" which are commonly in the neighborhood of one joule of energy or more in contrast to pacing pulses which are in the microjoule energy range.

In some situations, the electrical activity of the heart during ventricular fibrillation is at a very low amplitude level. If the implantable device tests whether the signal obtained from the heart, herein called a "cardiac signal", exceeds a threshold level, the device may diagnose a heart condition as asystole (no heartbeat) or bradycardia (slow heartbeat) and issue pacing pulses when, in fact, the heart is in ventricular fibrillation (VF) because the low level electrical activity indicative of VF is insufficient to trigger the threshold detection circuitry of the implantable device. Such pacing pulses could be detected by the sensing circuitry and further interfere with the recognition of the life-threatening ventricular fibrillation.

OBJECTS OF THE NEW INVENTION

It is an object of the present invention to provide an implantable device which is capable of sensing low level electrical cardiac signals before issuing pacing pulses to the heart.

It is another object of the present invention to utilize dual channel processing circuitry, one channel detecting the R-R interval and issuing a pacing signal (pacing channel) and the other channel (rate detect channel) having a variable amplifier with an automatic gain control to sense low level VF signals.

It is a further object of the present invention to blank the pacing signals for a short period of time in order to allow the gain in the heart rate detect channel to increase to such a level that low level VF cardiac signals can be detected.

SUMMARY OF THE INVENTION

The implantable cardioverter/pacer utilizes two channels respectively producing a pacing signal and a heart rate signal that are applied to a microprocessor. The pacer channel includes a sense amplifier which has a set gain and which triggers a one shot in the presence of the R-wave peak in the cardiac signal (ECG signal) applied to its input. The output of the one shot is applied to a pacer/timer which determines whether an R-wave is present within a pre-established time interval. When the R-wave is not detected, that is, when the one shot does not provide a reset pulse to the timer, the pacer/timer outputs a pacer signal to the microprocessor.

The rate detect channel obtains the cardiac or ECG signal in the same fashion as the pacer channel. That cardiac signal is initially amplified and then variably amplified utilizing an automatic gain control (AGC). The AGC will increase the gain of the controlled amplifier based upon the initial level of the cardiac signal and the time between detected peaks of the cardiac signal. The output of the variable gain amplifier is applied to a one shot which in turn produces heart rate signals to the microprocessor. The AGC has a time constant that is greater than the pacing escape interval or the time between normal sinus rhythm R-waves in the ECG or cardiac signal.

In order to detect low level VF cardiac signals, the microprocessor disregards or blanks out the first and possibly the second pacing signals from the pacer/timer in order to allow the gain in the rate detect channel to increase and approach a maximum value. When the gain in the rate detect channel is high, a determination can be made whether low level VF cardiac signals are present at the input or whether the heart is undergoing asystole or bradycardia. By ignoring or blanking out the pacing signals for a one or two second period, the rate detect channel does not detect any pacer artifacts and the microprocessor can apply the appropriate treatment to the heart either by issuing pacing pulses, if no low level VF cardiac signals are detected, or by issuing cardioverting pulses if VF is detected.

BRIEF DESCRIPTION OF THE DRAWINGS

Further objects and advantages of the present invention are found in the balance of this specification and in the accompanying drawings in which.

DETAILED DESCRIPTION

The present invention relates to an implantable cardioverter/pacer and particularly relates to a device which utilizes a pacing channel and a heart rate detect channel, the former issuing pacing signals when the R-R interval of the ECG or cardiac signal is not detected within a set time interval and the latter issuing heart rate signals even if the cardiac signal is only a low level electrical signal.

Figure 1:
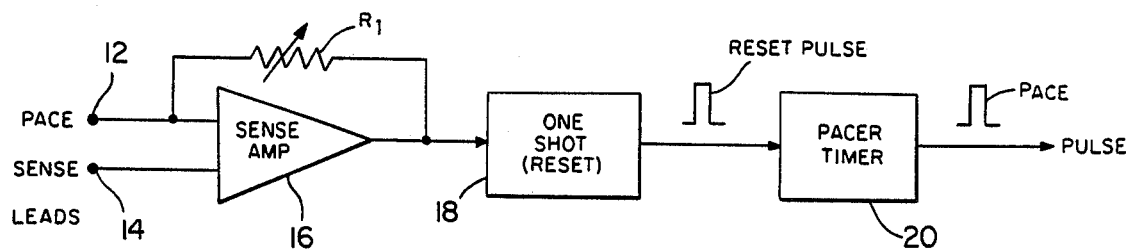
FIG. 1 illustrates the circuitry for providing a pacing pulse in a prior art device.

FIG. 1 illustrates in block diagram form a prior art device for determining whether an R-wave in the ECG or cardiac signal is present within a predetermined time interval and issuing a pacing pulse if such R-wave is not detected within the time interval. The ECG or cardiac signal is sensed by appropriate means attached to or proximate the heart of a patient such as a bipolar electrode lead, patch or combination thereof. The signal is applied to pace sense leads 12 and 14. Herein, the term "cardiac signal" is synonymous with the ECG signal. However, the cardiac signal may be an amplified version of the ECG signal. The cardiac signal from leads 12 and 14 is applied to sense amplifier 16 which is set by variable resistor R1. The output of amplifier 16 is applied to one shot 18 and when the amplitude of the cardiac signal exceeds a predetermined threshold, the output goes high and the one shot fires. One shot 18 produces a reset pulse of a predetermined duration at its output which is applied to the reset terminal of pacer timer 20. Pacer timer 20 is set to generate a pace pulse output if a reset pulse is not applied thereto within a predetermined time interval. This time interval defines a heartbeat rate level below which pacing pulses are applied to the heart. The interval can be set as can the amplification in sense amplifier 16. Generally, timer 20 times out shortly after the R-R interval during normal sinus rhythm or a normal heart beat.

In some situations, ventricular fibrillation is manifested only by fast rate, very low level electrical activity. If the low level cardiac signals are insufficient to exceed the trigger threshold of sense amplifier 16, the prior art pacing channel shown in FIG. 1 would result in a pace pulse being issued by pacer/timer 20 at each predetermined interval in the absence of a reset pulse from one shot 18. Accordingly, a control circuit which may be a microprocessor, would commonly react to the pace pulse by issuing pacing stimulating pulses to the heart since the microprocessor would not be provided with an indication of the low level ventricular fibrillation cardiac signal.

Figure 2:
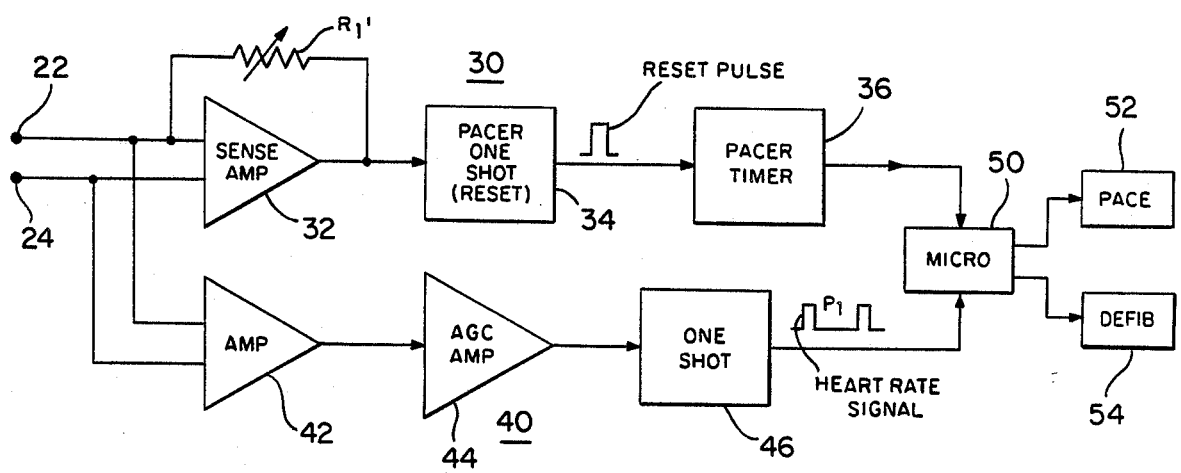
FIG. 2 illustrates, in block diagram form, the cardioverter/pacer in accordance with the principles of the present invention.

The present invention is schematically illustrated in FIG. 2 as a block diagram showing pacer channel 30 and rate detect channel 40, both receiving the cardiac signal from terminals 22 and 24.

Pacer channel 30 is generally similar to the circuit described above with respect to FIG. 1. Sense amplifier 32 has an adjustable sense level based upon the resistance of resistor R1'. The gain and the sense level of amplifier 32 is programmably set by a series of resistors that are represented by resistor R1'. Since amplifier 32 generates an output when the cardiac signal at leads 22 and 24 exceed the sense level, the adjustable level is desirable to avoid certain sensing signals such as the T-wave in the ECG signal, noise, etc. The input cardiac signal must exceed the threshold of sense amplifier 32 to trigger pacer one shot 34 to produce the reset pulse. A typical range to trigger sense amplifier 32 is from 0.5 mv to 5.0 mv. Below that threshold, one shot 34 does not fire or provide an output and hence pacer timer 36 times out and issues a pacing pulse to microprocessor control 50.

Since the VF cardiac signal amplitude can vary dramatically across the sensing leads (for example, a bipolar lead) which are electrically connected to input leads 22 and 24, the cardiac signal amplitude sometimes falls below the detectable threshold of pacer channel 30 and hence timer 36 times out and produces a pacing signal to microprocessor control 50.

Heart rate is one of the detection criteria for diagnosing ventricular fibrillation. Therefore, it is necessary to measure cardiac activity below the pace sensitivity threshold. Rate detect channel 40 in FIG. 2 produces a heart rate signal for microprocessor 50 notwithstanding the level of the cardiac input signal applied to leads 22 and 24.

Rate detect channel 40 includes amplifier 42 for preamplifying the cardiac signal, amplifier 44 which includes an automatic gain control (herein AGC), and one shot 46 that provides an output indicative of the heart rate. Interval $P_1$ is the R-R interval of the ECG or cardiac signal detected by rate detect channel 40. Rate detect channel 40 can also include a comparator or threshold sensor intermediate amplifier 44 and one shot 46 such that a signal is only applied to the one shot if it exceeds the reference or threshold. Alternatively, the one shot can be set only to trigger when the input signal exceeds a minimum threshold value.

Generally, the cardiac signal is amplified in amplifier 42, and then is variably amplified in amplifier 44. The gain in amplifier 44 is set by the AGC and is based upon the initial level of the cardiac signal applied thereto as well as the time between the peaks of that initial signal. When the further amplified cardiac exceeds a threshold, a signal is applied to one shot 46 and a pulse is generated therefrom indicating the heartbeat rate.

Figure 3:
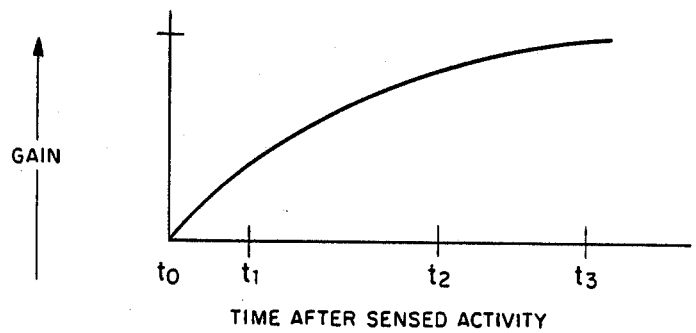
FIG. 3 illustrates a graph showing the increase in gain of the rate detect channel versus time in accordance with the principles of the present invention.

FIG. 3 shows the gain versus time after sensed activity curve for the AGC in FIG. 2. The AGC has an inherent time constant required for maximum sensitivity. The time constant of the AGC is longer than the typical pacing interval or the R-R interval. The principal reason for this long time constant is to avoid sensing unwanted cardiac activity that may create a false indication of ventricular tachycardia or ventricular fibrillation. Times $t_1$, $t_2$ and $t_3$ in FIG. 3 correspond to the time span from the reset state $t_0$ of the AGC. The AGC is reset based upon the time of the last sensed peak and the amplitude of that peak. Therefore, at time $t_0$, the AGC is reset due to a normal R-wave in the cardiac signal. Time $t_1$ may correspond to one-half of the R-R interval. Time $t_2$ may correspond to two or three times the R-R interval and time $t_3$ may correspond to three or four times the R-R interval. Of course, if no signal is sensed until time $t_2$, the gain of amplifier 44 is approaching a maximum.

Figure 4:
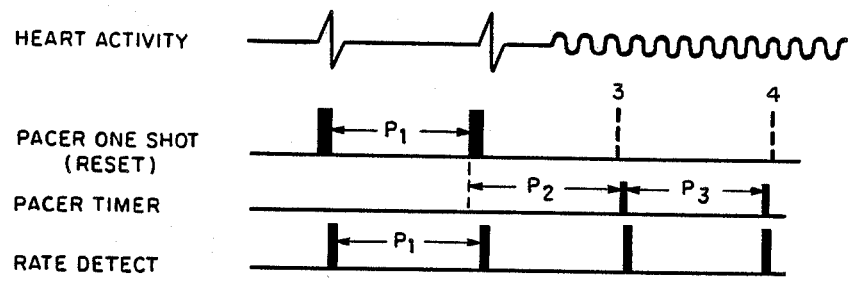
FIG. 4 illustrates a timing diagram showing the rate detect channel sensing the artifact of the pacing pulses applied to the heart.

FIG. 4 shows a timing diagram wherein the heart activity time line, or an exemplary ECG signal, shows sudden onset of ventricular fibrillation wherein the electrical signal level of the VF is very low compared to the amplitude of the R-wave. Pacer one shot 34 issues a reset pulse at each detected R-wave as shown in FIG. 4. Therefore, pacer timer 36 is reset after interval P1.

However, after that interval pacer timer 36 times out at the end of interval P2 and issues a pacing signal to microprocessor 50. Timer 36 is then automatically reset, continues to count down and issues another pacing signal at the end of interval P3. In prior art devices, microprocessor 50 would activate pacemaker circuit 52 and circuit 52 would issue pacing pulses to the heart. These pacing pulses stimulate the heart and the artifacts of the pulses cause rate detect channel 40 to produce a heart rate signal at the end of interval P2 as well as interval P3. Therefore microprocessor 50 possibly would not be capable of detecting the very fast but low level cardiac activity indicative of some types of VF.

Figure 5:
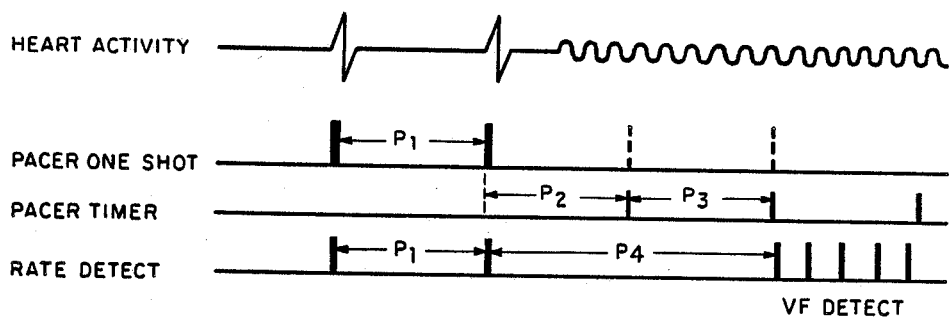
FIG. 5 shows a timing diagram wherein the pacing signals are blanked out for a period of time in order to detect low level VF cardiac signals.

FIG. 5 illustrates the same heart activity or cardiac signal, the resulting output of pacer one shot 34 and the resulting output of pacer timer 36. However, in FIG. 5, the pacing signals are blanked out or ignored by microprocessor 50 for a two second period (as an example) such that the AGC increases the gain of amplifier 44 in rate detect channel 40 and hence heart rate signals are applied to microprocessor 50 at the end of prolongation interval P4. In this particular case, the first two pacer signals were blanked out such that microprocessor 50 could "look at" the heart rate signal from rate detect channel 40 before issuing pacing pulses to the heart. Subsequent to interval P4, microprocessor 50 could determine the appropriate treatment to be applied to the heart, i.e., low level cardioverting pulse from defibrillating (or cardioverting) circuit 54, high level cardioverting pulse, a certain pacing pulse routine, or combination thereof in order to treat the VF.

Figure 6:
FIG. 6 shows the prolongation of the heart rate as an electrocardiogram signal (herein ECG) in accordance with the principles of the present invention; and, FIGS. 7, 8, 9 and 10 show timing diagrams wherein the blanking period is utilized only once and for a certain number of time intervals thereafter, a pacing pulse is issued if the R-wave is not detected within each such interval.

FIG. 6 shows the ECG signal of a heart that is subject to bradycardia (low heartbeat rate). If the blanking period is one or two seconds, the heart beat will only be prolonged a relatively short period of time before pacing pulses are issued by pace circuit 52. After the blanking period, and in the presence of further pacing signals applied to microprocessor 50, the microprocessor is programmed to issue regular stimulating pacing pulses pulses to the heart based upon the pacing signal applied thereto from pacer timer 36.

Figure 7:
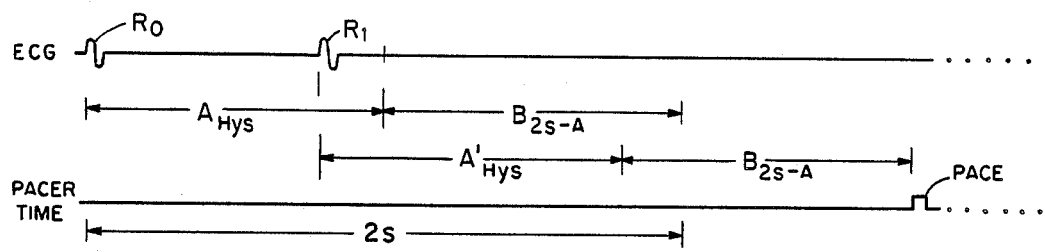

The microprocessor can also be programmed to blank out the pacing signal only once and issue pacing pulses, through pacer circuit 52, if the heart beat rate remains below a predetermined level. FIGS. 7 through 10 show timing diagrams describing the operation of such a program. In one embodiment, the pacer channel is used to monitor heart activity for the pacemaker function. The rate detect channel monitors the heart for tachycardia. If the rate on the pacer channel is above the hysteresis rate or the predetermined low level heart beat rate, the heart will not be paced. In FIG. 7, the time interval between R-wave $R_0$ and wave $R_1$ in the ECG signal is less than the hysteresis rate designated by interval $A_{Hys}$. Interval $B_{2S-A}$ is the remainder of the two second blanking interval for the pacing signal in this embodiment. In general, if the rate falls below the hysteresis rate as is shown in FIG. 7, after $R_1$, the heart will be paced at the bradycardia pacing rate. However, before a pacing pulse is issued as the rate decreases below the hysteresis rate level, two seconds must elapse as shown in the time line. If an R-wave is not detected on the pacing channel prior to the first hysteresis timeout, a two second time out is initiated. If an R-wave is not detected during the two second timeout ($A'_{Hys}+B_{S-A}$), a pace will be issued after the two second timeout, i.e., at the end of $B_{2S-A}$. If intrinsic heart activity stays below the bradycardia rate or hysteresis rate, the heart will be paced at the bradycardia pacing rate.

Figure 8:
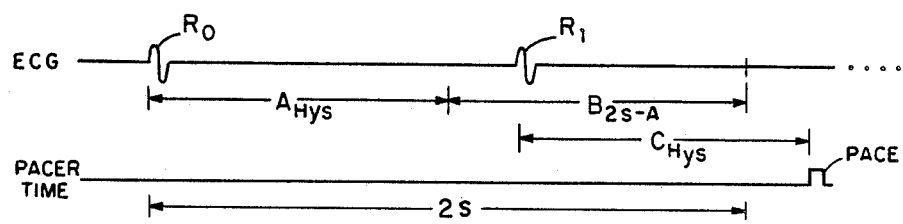

If an R-wave is detected during the two second interval as shown in FIG. 8 (See $R_1$), one additional hysteresis interval $C_{Hys}$ will be timed out. If no R-wave is detected during this interval the heart will be paced at the end of the interval if the total time exceeds two seconds.

Figure 9:
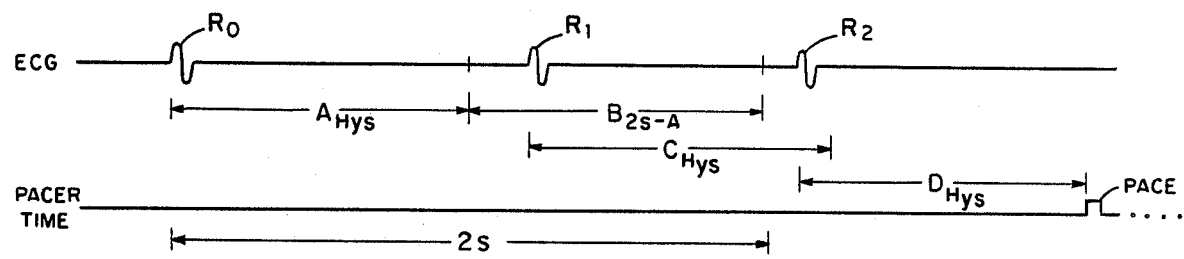
Figure 10:
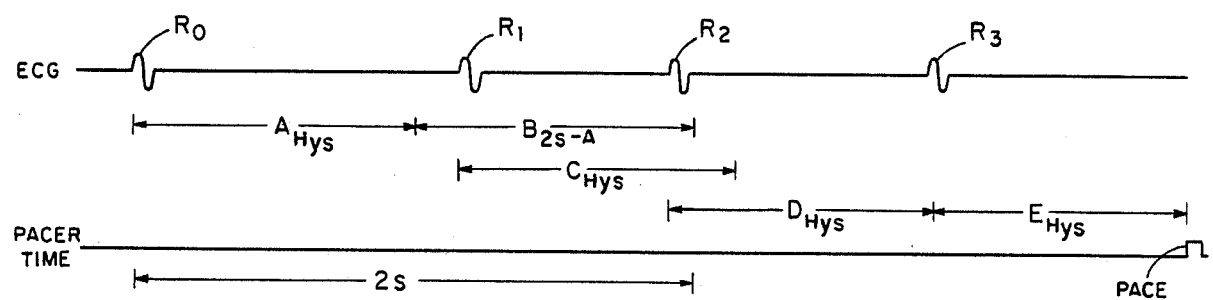

Additional single hysteresis intervals will be timed out unless four consecutive R-waves are detected that indicate a rate greater than the hysteresis rate, i.e., the R-waves fall within the hysteresis rate interval. If this happens, the two second interval timeout before pacing will be reinitiated. FIG. 9 shows wave $R_1$ within the two second period and wave $R_2$ within hysteresis interval $C_{Hys}$ but no other R-wave within the next interval $D_{Hys}$; therefore, a pacing pulse is issued at the end of $D_{Hys}$ without recalling the blanking period. FIG. 10 shows waves $R_2$ and $R_3$ in intervals $C_{Hys}$ and $D_{Hys}$ respectively but a pacing pulse is issued at the end of interval $E_{Hys}$ because of the absence of an R-wave during that time interval. In order to reinstate the two second blanking period, an R-wave would have to be detected during intervals $C_{Hys}$, $D_{Hys}$, $E_{Hys}$ and $F_{Hys}$ in order to reset the microprocessor.

While only certain preferred features of the invention have been shown by way of illustration, many modifications and changes can be made. It is to be understood that the appended claims are intended to cover all such modifications and changes as fall within the true spirit and scope of the invention.

What is claimed is:

1. An implantable system including pacing and cardioverting capabilities for detecting abnormal heart rates by sensing the electrical activity of the heart and stimulating the heart accordingly, the system comprising:

sensing means for sensing said electrical activity of the heart and for carrying a cardiac signal indicative thereof;

time and amplitude determining means connected to said sensing means for issuing a pacer signal when the amplitude of said cardiac signal fails to exceed a first predetermined threshold within a predetermined time period;

amplifying and detection means connected to said sensing means for amplifying said cardiac signal and producing a heart rate signal when the amplified cardiac signal exceeds a second predetermined threshold, said amplifying and detection means including an automatic gain control for variable amplifying said cardiac signal, said automatic gain control being reset by the amplitude of said cardiac signal and includes an inherent time constant;

said system including a heart condition detection means connected to said time and amplitude determining means and to said amplifying and detection means for receiving said pacer signal and said heart rate signal, said heart condition detection means ignoring the occurrence of said pacer signal for a set period of time such that the gain of the automatic gain control increases with time based upon said amplitude of said cardiac signal for further amplifying said heart rate signal; and, stimulating means connected to said heart condition detection means for stimulating said heart based upon said pacer signal and said heart rate signal.

2. A system as claimed in claim 1 wherein said means for stimulating includes means for generating pacing pulses dependent upon said pacer signal, means for generating further heart stimulating pulses dependent upon said heart rate signal and means for delaying the application of said pacing pulses until the gain in said amplifying portion of said amplifying and detection means approaches a maximum value.

3. A system as claimed in claim 2 wherein said maximum value of said gain of said automatic gain control is sufficient to amplify low level cardiac signals signals caused by said heart during ventricular fibrillation.

4. A system as claimed in claim 2 wherein said time and amplitude determining means comprises a pacing detection channel that includes a threshold determining means for determining when the cardiac signal reaches a predetermined value and generating an output signal, and an timing means for issuing said pacer signal when said output signal is not applied thereto within a said predetermined time period; said amplifying and detection means comprises a rate detection channel that includes an amplifier having a set gain for amplifying said cardiac signal, a second amplifier having an adjustable gain that is controlled by said automatic gain control for variably amplifying further said cardiac signal, means for determining when the further amplified cardiac signal reaches a set value for generating said heart rate signal.

5. A system as claimed in claim 2 wherein the time constant of said automatic gain control is greater than a pacing escape interval.

6. An implantable system including pacing and cardioverting capabilities for detecting and treating an abnormal heart by sensing the electrical activity of the heart and stimulating the heart accordingly, the system comprising:

sensing means for sensing said electrical activity of the heart and for carrying a cardiac signal indicative thereof;

time and amplitude determining means connected to said sensing means for issuing a pacer signal when the amplitude of said cardiac signal fails to exceed a first predetermined threshold within a predetermined time period;

amplifying and detection means connected to said sensing means for amplifying said cardiac signal and producing a heart rate signal when the amplified cardiac signal exceeds a second predetermined threshold, said amplifying and detection means including an automatic gain control for variably amplifying said cardiac signal, said automatic gain control being reset by the amplitude of said cardiac signal and includes an inherent time constant;

said system including a heart condition detection means connected to said time and amplitude determining means and said amplifying and detection means for receiving said pacer signal and said heart rate signal, said heart condition detection means ignoring the occurrence of said pacer signals for a set period of time such that the gain of said automatic gain control increases with the time based upon said amplitude of said cardiac signal for further amplifying said heart rate signal; and, stimulating means connected to said heart condition detection means for stimulating said heart based upon said pacer signal and said heart rate signal and generating pacing pulses only after said set time period has elapsed in order to allow said gain of said automatic gain control to approach a maximum level such that low level cardiac signals, that are indicative of some types of ventricular arrhythmias, can be detected by said amplifying and detection means and the resulting heart rate signal utilized as a basis for treatment of the heart.

7. The system as claimed in claim 6 wherein said means for stimulating includes a delay means that postpones application of said pacing pulses until said heart condition detection means, connected to said amplifying and detection means, receiving said heart rate signal, determines that said heart is not in one of said ventricular arrhythmias.

8. The system as claimed in claim 7 wherein said means for stimulating includes means for delivering one or more cardioverting pulses to said heart as a consequence of determining one of said ventricular arrhythmias by said heart condition detection means.

9. A system as claimed in claim 6 including means for activating said means for stimulating and generating pacing pulses based upon the occurrence of said pacer signal after an initial lapse of said set time period unless said pacer signals are not generated for a period of time greater than said set period and greater than a plurality of predetermined time periods.

10. A method of detecting and treating abnormal heart rates with an implantable device having cardioverting and pacing capabilities by sensing the electrical activity of the heart and treating the heart by applying stimulation thereto, the method comprising the steps of:

obtaining a cardiac signal indicative of said electrical activity of the heart;

generating a pacer signal when said cardiac signal fails to exceed a preestablished threshold within a predetermined time period;

variably amplifying said cardiac signal such that the level of amplification of said cardiac signal increases with time and is based upon the initial level of said cardiac signal;

determining when the amplified cardiac signal reaches a second predetermined threshold and generating a heart rate signal; and, ignoring said pacer signal for a set period of time in order to allow said cardiac signal to be amplified to a detectable level such that the low level cardiac signals, that are indicative of some types of ventricular arrhythmias, can be detected; for stimulating the heart accordingly, otherwise, stimulating the heart based upon said pacer signals and said heart rate signals.

11. An implantable system including pacing and cardioverting capabilities for detecting abnormal heart rates by sensing the electrical activity of the heart and stimulating the heart accordingly, the system comprising:

sensing means for sensing said electrical activity of the heart and for carrying a cardiac signal indicative thereof;

time and amplitude determining means connected to said sensing means for issuing a pacer signal when the amplitude of said cardiac signal fails to exceed a first predetermined threshold within a predetermined time period;

amplifying and detection means connected to said sensing means for amplifying said cardiac signal and producing a heart rate signal when the amplified cardiac signal exceeds a second predetermined threshold, said amplifying and detection means including an automatic gain control, the gain of said automatic gain control increasing with time based upon the amplitude of said cardiac signal; and, means for stimulating said heart based upon said pacer signal and said heart rate signal, including means for generating pacing pulses dependent upon said pacer signal, means for generating further heart stimulating pulses dependent upon said heart rate signal and means for delaying the application of said pacing pulses until the gain of said automatic gain control of said amplifying and detection means approaches a maximum value.

12. A system as claimed in claim 11 wherein said maximum value of said gain of said automatic gain control is sufficient to amplify low level cardiac signals caused by said heart during ventricular fibrillation.

13. A system as claimed in claim 11 wherein said time and amplitude determining means comprises a pacing detection channel that includes a threshold determining means for determining when the cardiac signal reaches a predetermined value and generating an output signal, and a timing means for issuing said pacer signal when said output signal is not applied thereto within a said predetermined time period; said amplifying and detection means comprises a rate detection channel that includes an amplifier having a set gain for amplifying said cardiac signal, a second amplifier having an adjustable gain that is controlled by said automatic gain control for variably amplifying further said cardiac signal, means for determining when the further amplified cardiac signal reaches a set value for generating said heart rate signal.

14. A system as claimed in claim 11 wherein the time constant of said automatic gain control is greater than a pacing escape interval.

15. An implantable system including pacing and cardioverting capabilities for detecting and treating an abnormal heart by sensing the electrical activity of the heart and stimulating the heart accordingly, the system comprising:

sensing means for sensing said electrical activity of the heart and for carrying a cardiac signal indicative thereof;

time and amplitude determining means connected to said sensing means for issuing a pacer signal when the amplitude of said cardiac signal fails to exceed a first predetermined threshold within a predetermined time period;

amplifying and detection means connected to said sensing means for amplifying said cardiac signal and producing a heart rate signal when the amplified cardiac signal exceeds a second predetermined threshold, said amplifying and detection means including an automatic gain control, the gain of said automatic gain control increasing with time based upon the amplitude of said cardiac signal; and, means for stimulating said heart based upon said pacer signal and said heart rate signal and generating pacing pulses only after a set time period has elapsed in order to allow said gain in said amplifying portion to approach a maximum level such that low level cardiac signals, that are indicative of some types of ventricular arrhythmias, can be detected by said amplifying and detection means and the resulting heart rate signal utilized as a basis for treatment of the heart, said means for stimulating including a delay means that postpones application of said pacing pulses until a heart condition detection means, connected to said amplifying and detection means for receiving said heart rate signal, determines that said heart is not in one of said ventricular arrhythmias.

16. The system as claimed in claim 15 wherein said means for stimulating includes means for delivering one or more cardioverting pulses to said heart as a consequence of determining one of said ventricular arrhythmias by said heart condition detection means.

17. An implantable system including pacing and cardioverting capabilities for detecting and treating an abnormal heart by sensing the electrical activity of the heart and stimulating the heart accordingly, the system comprising:

sensing means for sensing said electrical activity of the heart and for carrying a cardiac signal indicative thereof;

time and amplitude determining means connected to said sensing means for issuing a pacer signal when the amplitude of said cardiac signals fails to exceed a first predetermined threshold within a predetermined time period;

amplifying and detection means connected to said sensing means for amplifying said cardiac signal and producing a heart rate signal when the amplified cardiac signal exceeds a second predetermined threshold, said amplifying and detection means including an automatic gain control, the gain of said automatic gain control increasing with time based upon the amplitude of said cardiac signal; and, means for stimulating said heart based upon said pacer signal and said heart rate signal and generating pacing pulses only after a set time period has elapsed in order to allow said gain in said amplifying portion to approach a maximum level such that low level cardiac signals, that are indicative of some types of ventricular arrhythmias, can be detected by said amplifying and detection means and the resulting heart rate signal utilized as a basis for treatment of the heart;

said system including means for activating said means for stimulating and generating pacing pulses based upon the occurrence of said pacer signal after an initial lapse of said set time period unless said pacer signals are not generated for a period of time greater than said set period and greater than a plurality of predetermined time periods.

* * * * *